(12) United States Patent
Hesse et al.

(10) Patent No.: US 6,967,195 B2
(45) Date of Patent: Nov. 22, 2005

(54) 2-SUBSTITUTED PREGNA-1-3,5(10) TRIENE AND CHOLA-1,3,5(10) TRIENE DERIVATIVES AND THEIR BIOLOGICAL ACTIVITY

(75) Inventors: Robert Henry Hesse, Winchester, MA (US); Sundara Katugam Srinivasasetty Setty, Cambridge, MA (US); Maurice Murdoch Pechet, Cambridge, MA (US); Michael Gile, Methuen, MA (US)

(73) Assignee: Research Institute for Medicine and Chemistry, Inc., Cambridge, MA (US)

( * ) Notice: Subject to any disclaimer, the term of this patent is extended or adjusted under 35 U.S.C. 154(b) by 0 days.

(21) Appl. No.: 10/275,257

(22) PCT Filed: May 11, 2001

(86) PCT No.: PCT/GB01/02103

§ 371 (c)(1),
(2), (4) Date: Mar. 13, 2003

(87) PCT Pub. No.: WO01/85755

PCT Pub. Date: Nov. 15, 2001

(65) Prior Publication Data

US 2003/0158167 A1 Aug. 21, 2003

Related U.S. Application Data

(60) Provisional application No. 60/203,462, filed on May 11, 2000.

(51) Int. Cl.[7] .............................. A61K 31/56; C07J 9/00
(52) U.S. Cl. ...................... 514/182; 552/541; 552/548; 552/553; 552/555
(58) Field of Search ....................... 514/182; 552/541, 552/548, 553, 555

*Primary Examiner*—Barbara P. Badio
(74) *Attorney, Agent, or Firm*—Bacon & Thomas

(57) ABSTRACT

Compounds of formula (I) in which: $R^1$ represents a hydrogen atom or an O-protecting group; $R^2$ represents a hydroxyl, lower alkoxy, carboxaldehyde, lower alk-1-enyl or hydroxy- or lower alkoxy-substituted lower alkyl group; $R^3$ represents a methyl group having α- or β-configuration; X represents a $C_{1-3}$ alkylene group or a valence bond; Y represents a carboxaldehyde group or a group of formula —$C(R^4)(R^5)OR^1$ where $R^1$ is as defined above and $R^4$ and $R^5$, which may be the same or different, are each selected from hydrogen atoms, alkyl, alkenyl and alkynyl groups such that the total carbon content of $R^4$ and $R^5$ does not exceed three atoms, with the proviso that X is a valence bond when both $R^4$ and $R^5$ are other than hydrogen; and the dotted line signifies that a double bond may optionally be present at the 16(17)-position exhibit potent cell modulating activity, including antiproliferative and antiangiogenic effects.

10 Claims, No Drawings

2-SUBSTITUTED PREGNA-1-3,5(10) TRIENE AND CHOLA-1,3,5(10) TRIENE DERIVATIVES AND THEIR BIOLOGICAL ACTIVITY

CROSS REFERENCE OF RELATED APPLICATIONS

This application is a 371 of PCT/GB01/02103, filed May 11, 2001 which claims benefit of U.S. provisional application Ser. No. 60/203,462, filed May 11, 2000.

This invention relates to novel sterol derivatives, more particularly to 2-substituted ring A aromatic sterol derivatives having a comparatively short 17-position hydrocarbyl side chain which terminates in an carboxaldehyde group or an optionally substituted hydroxyl group. Such compounds have been found to have cell modulating activity and may exhibit valuable antiproliferative and antiangiogenic effects.

WO-A-0068246 discloses a range of 3-sterols and O-protected derivatives having an aromatic A-ring and a 17-position side chain which terminates with an amine, amide or hydroxyl group attached to a tertiary carbon atom. These compounds exhibit potent effects on the modulation of cell growth and differentiation, for example as demonstrated by their ability to inhibit growth of cancer cells in vitro and in vivo, while possessing an advantageous therapeutic ratio by virtue of their low levels of calcaemic activity, for example as determined by their effects on serum calcium and phosphorus levels in rats. In this respect the activity of the compounds resembles that of various vitamin D analogues despite the fact that they have an intact tetracyclic nucleus and lack both the seco steroid triene system of vitamin D analogues and the ability to mimic a conjugated conformational isomer thereof.

It is also known that 2-methoxyoestradiol, which like 2-methoxyoestrone is a natural metabolite of oestradiol, prevents proliferation and promotes the death of cancer cells in vivo. Studies have suggested that these effects are at least in part mediated by inhibition or misdirection of tubulin polymerisation in a manner similar to that exhibited by colchicine; thus the metabolite has been observed to bind to the colchicine binding site of tubulin.

As noted by Cushman et al. in *J. Med. Chem.* 38(12), pp. 2041–2049 [1995], 2-methoxyoestradiol has also been found to inhibit angiogenesis (the creation of new blood vessels); this is potentially an extremely valuable property in cancer treatment, since angiogenesis is required for the growth of solid tumours. Both Cushman et al. (op. cit.) and Lovely et al. in *J. Med. Chem.* 39(9), pp. 1917–1923 [1996] report the synthesis and evaluation for cytotoxicity of various 2-methoxyoestradiol analogues; all the compounds investigated were 17-ones or optionally substituted 17-ols.

The antiproliferative and antiangiogenic effects of 2-methoxyoestradiol are discussed by Pribluda et al. in *Cancer and Metastatic Reviews* 19(1–2), pp. 173–179 [2000], where it is stated that it targets both tumour cell and endothelial cell compartments by inducing apoptosis in rapidly proliferating cells and inhibiting blood vessel formation at several stages in the angiogenic cascade. It is also said to inhibit metastatic spread in several models.

Dubey et al. in *Biochem. Biophys. Comm.* 278(1), pp. 27–33 [2000] report that endogenous methoxyoestradiols mediate the antimitogenic effects of oestradiol on vascular smooth muscle cells via oestrogen receptor-independent mechanisms.

WO-A-9933859 discloses a variety of 1,3,5-oestratrienes having heteroatom-containing hydrocarbyl side chains at the 17-position. The compounds are said to be oestrogen antagonists and there is no suggestion that they may exhibit antiproliferative or antiangiogenic effects or colchicine-like interference with tubulin polymerisation.

WO-A-9933858 discloses 3-sulphamoyloxy-1,3,5-oestratrienes which contain relatively short hydrocarbyl side chains at the 17-position and which are said to act as inhibitors of steroidal sulphatase enzymes. Again there is no suggestion that they may exhibit antiproliferative or antiangiogenic effects or colchicine-like interference with tubulin polymerisation.

The present invention is based on the unexpected finding that a range of 2-substituted ring A aromatic sterol derivatives having a comparatively short 17-position hydrocarbyl side chain which terminates in a carboxaldehyde (—CHO) group or an optionally O- and/or C-substituted hydroxymethyl group exhibit potent cell modulating activity. Tissue culture assays show such compounds to exhibit dose response curves characteristic of colchicine, suggesting that their antiproliferative activity derives at least in part from colchicine-like interference with tubulin polymerisation. Compounds of the invention may therefore inhibit angiogenesis in analogous but more potent manner compared to compounds such as 2-methoxyoestradiol. The compounds also show reduced but still significant binding to oestrogen receptors, suggesting that they may have further applications analogous to those of other non-uterotrophic oestrogen response modulators.

According to one embodiment of the invention there are provided compounds of formula (I)

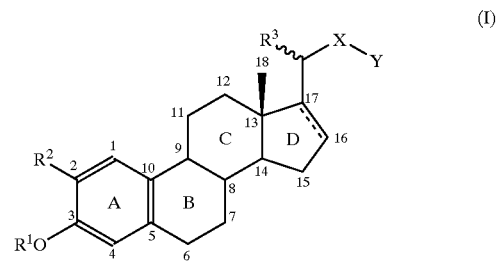

in which:

$R^1$ represents a hydrogen atom or an O-protecting group;

$R^2$ represents a hydroxyl, lower alkoxy, carboxaldehyde, lower alk-1-enyl or hydroxy- or lower alkoxy-substituted lower alkyl group;

$R^3$ represents a methyl group having α- or β-configuration;

X represents a $C_{1-3}$ alkylene group or a valence bond;

Y represents a carboxaldehyde group or a group of formula —$C(R^4)(R^5)OR^1$ where $R^1$ is as defined above and $R^4$ and $R^5$, which may be the same or different, are each selected from hydrogen atoms, alkyl, alkenyl and alkynyl groups such that the total carbon content of $R^4$ and $R^5$ does not exceed three atoms, with the proviso that X is a valence bond when both $R^4$ and $R^5$ are other than hydrogen; and the dotted line signifies that a double bond may optionally be present at the 16(17)-position.

O-protecting groups present as $R^1$ groups may, for example, comprise any suitable cleavable O-protecting group such as is known in the art. Representative groups include (i) etherifying groups such as silyl groups (e.g. tri(lower alkyl)silyl groups such as trimethylsilyl, triethylsilyl, triisopropylsilyl or t-butyldimethylsilyl; tri(aryl)silyl groups such as triphenylsilyl; and mixed alkylarylsilyl groups), lower (e.g. $C_{1-6}$) alkyl groups optionally interrupted by an oxygen atom (e.g. such as methyl, ethyl, methoxymethyl or methoxyethoxymethyl) or substituted by a lower (e.g. $C_{3-8}$) cycloalkyl group (e.g. as in cyclopentylmethyl) or by an acyloxy group (e.g. by a lower alkanoyloxy group, for example as in pivaloyloxymethyl), and cyclic ether groups (e.g. such as tetrahydropyranyl), and (ii) esterifying groups such as lower (e.g. $C_{1-6}$) alkanoyl (e.g. such as acetyl, propionyl, isobutyryl, pivaloyl or hemisuccinyl), aroyl (e.g. containing 7–15 carbon atoms, such as benzoyl or 4-phenylazobenzoyl), lower (e.g. $C_{1-6}$) alkane sulphonyl (e.g. such as methane sulphonyl or halogenated methane sulphonyl), arene sulphonyl (e.g. such as p-toluene sulphonyl), and sulphamoyl, for example groups of formula $(R^6)(R^7)N.SO_2$— where $R^6$ and $R^7$ are each independently selected from hydrogen atoms and lower (e.g. $C_{1-6}$) alkyl groups or together form a lower (e.g. $C_{3-10}$) alkylene chain optionally interrupted by one or more heteroatoms selected from O, N and S. It will be appreciated that $R^1$ at the 3-position may be the same as or different from any $R^1$ the 17-position side chain.

Where $R^2$ represents a lower alkoxy group, this may for example be a straight chain or branched $C_{1-6}$ alkoxy group such as a methoxy, ethoxy or propoxy group. Lower alk-1-enyl groups may, for example, contain 2–6 carbon atoms, e.g. as in vinyl, prop-1-enyl and but-1-enyl groups. Representative hydroxy- and lower alkoxy-substituted lower alkyl groups include hydroxymethyl, 1- and 2-hydroxyethyl, 1-, 2- and 3-hydroxypropyl and corresponding methoxy- and ethoxy-substituted groups. Lower alkoxy-substituted lower alkyl groups preferably contain up to 6 carbon atoms in total.

Where $R^3$ in formula (I) is a methyl group in the α-configuration, the compounds have the 20R configuration characteristic of natural sterols such as cholesterol; where $R^3$ is in the β-configuration the compounds have the 20S configuration of the corresponding epi-derivatives. It will be appreciated that the invention also embraces mixtures of the two isomers.

Where X is an alkylene group this may, for example, be a methylene, ethylene or trimethylene group.

Where Y represents a group of formula —$C(R^4)(R^5)OR^1$ this may advantageously be an optionally O-protected hydroxymethyl group or a substituted hydroxymethyl group in which one of $R^4$ and $R^5$ is methyl, ethyl, vinyl, ethynyl or propargyl and the other is hydrogen, or in which $R^4$ and $R^5$ are both methyl.

Compounds of formula (I) in which $R^1$ is hydrogen, a metabolically labile O-protecting group (e.g. a lower alkanoyl group such as acetyl or hemisuccinyl; an acyloxymethyl group, for example a lower alkanoyloxymethyl group such as pivaloyloxymethyl; or a sulphonyl group, for example as in a sulphate or sulphamate group) or a lower alkyl etherifying O-protecting group such as methyl, ethyl or isobutyl may be useful directly in therapy. The use of compounds in which $R^1$ is a biolabile sulphamoyl group may be advantageous, since such groups will tend to inhibit steroid sulphatases which may otherwise degrade steroid-3-ols formed upon removal of such a protecting group from the 3-position. Compounds (I) containing non-metabolically labile O-protecting groups (e.g. bulky silyl ether groups such as triisopropyl, t-butyldimethylsilyl or triphenylsilyl) are principally of use as synthetic intermediates.

The cell modulating activity of active compounds according to the invention, combined with their substantial lack of adverse side effects, render them of interest both alone and as adjuncts in the management of diseases associated with abnormal cell proliferation, such as neoplastic disease, particularly myelogenous leukemias as well as neoplastic disease of the brain, breast, stomach, gastrointestinal tract, prostate, pancreas, uro-genital tract (male and female) and pulmonary neoplasia. Their ability to promote closure of mouse ear puches suggests their use, either alone or as adjuncts, as agents to promote wound healing.

Their cell modulating activity suggests that active compounds of the invention may, like other oestrogen response modulators, have additional utilities either alone or as adjuncts in the chemotherapy of infection and in other therapeutic modalities in which mononuclear phagocytes are involved, for example in treatment of bone disease (especially osteoporosis, osteopenia and osteodystrophy as in rickets or renal osteodystrophy), autoimmune disease, host-graft reaction, transplant rejection, inflammatory diseases (including modulation of immunoinflammatory reactions), neoplasias and hyperplasias, their potential utility in treatment of neoplasias and hyperplasias being evidenced by their ability to inhibit growth of a variety of human cancer cells. Additionally, they may be useful in treatment of dermatological diseases (for example including acne, alopecia, eczema, pruritus, psoriasis and skin aging, including photoaging), hypertension, rheumatoid arthritis, psoriatic arthritis, asthma, cognitive impairment and senile dementia (including Alzheimer's disease), in fertility control in both human and animal subjects, in lowering elevated serum cholesterol, and in management of disorders involving blood clotting (e.g. by dissolution of existing clots and/or by prevention of clotting). The invention embraces use of these compounds in the therapy or prophylaxis of such conditions and in the manufacture of medicaments for use in such treatment or prophylaxis.

Active compounds according to the invention may be formulated for administration by any convenient route, e.g. orally (including sublingually), parenterally, rectally or by inhalation; pharmaceutical compositions so formulated comprise a feature of the invention.

Orally administrable compositions may, if desired, contain one or more physiologically compatible carriers and/or excipients and may be solid or liquid. The compositions may take any convenient form including, for example, tablets, coated tablets, capsules, lozenges, aqueous or oily suspensions, solutions, emulsions, syrups, elixirs and dry products suitable for reconstitution with water or another suitable liquid vehicle before use. The compositions may advantageously be prepared in dosage unit form. Tablets and capsules according to the invention may, if desired, contain conventional ingredients such as binding agents, for example syrup, acacia, gelatin, sorbitol, tragacanth or polyvinyl-pyrollidone; fillers, for example lactose, sugar, maize-starch, calcium phosphate, sorbitol or glycine; lubricants, for example magnesium stearate, talc, polyethylene glycol or silica; disintegrants, for example potato starch; or acceptable wetting agents such as sodium lauryl sulphate. Tablets may be coated according to methods well known in the art.

Liquid compositions may contain conventional additives such as suspending agents, for example sorbitol syrup, methyl cellulose, glucose/sugar syrup, gelatin, hydroxymethylcellulose, carboxymethylcellulose, aluminium stearate gel or hydrogenated edible fats; emulsifying agents, for example lecithin, sorbitan monooleate or acacia; non-aqueous vehicles, which may include edible oils, for example vegetable oils such as arachis oil, almond oil, fractionated coconut oil, fish-liver oils, oily esters such as polysorbate 80, propylene glycol, or ethyl alcohol; and preservatives, for example methyl or propyl p-hydroxybenzoates or sorbic acid. Liquid compositions may conveniently be encapsulated in, for example, gelatin to give a product in dosage unit form.

Compositions for parenteral administration may be formulated using an injectable liquid carrier such as sterile pyrogen-free water, sterile peroxide-free ethyl oleate, dehydrated alcohol or propylene glycol or a dehydrated alcohol/propylene glycol mixture, and may be injected intravenously, intraperitoneally or intramuscularly.

Compositions for rectal administration may be formulated using a conventional suppository base such as cocoa butter or another glyceride.

Compositions for administration by inhalation are conveniently formulated for self-propelled delivery, e.g. in metered dose form, for example as a suspension in a propellant such as a halogenated hydrocarbon filled into an aerosol container provided with a metering dispense valve.

It may be advantageous to incorporate an antioxidant, for example ascorbic acid, butylated hydroxyanisole or hydroquinone in the compositions of the invention to enhance their storage life.

Where any of the above compositions are prepared in dosage unit form these may for example contain 2 µg–100 mg of active compound according to the invention per unit dosage form; such dosage units may for example be administered 1–4 times per day. The compositions may if desired incorporate one or more further active ingredients.

A suitable daily dose of an active compound according to the invention may for example be in the range 2 µg–400 mg per day, depending on factors such as the severity of the condition being treated and the age, weight and condition of the subject.

Compounds according to the invention may be prepared by any convenient method, for example by reaction of a compound containing a precursor for the desired 17-position side chain in one or more stages and with one or more reactants serving to form the desired 17-position side chain, followed if necessary and/or desired by removal of any O-protecting group(s).

Thus, for example, compounds of the invention may be prepared from appropriately 2-substituted, e.g. 2-hydroxylated or 2-alkoxylated, derivatives of oestrone by, for example, Wittig reaction with an ethylidene phosphorane to convert the 17-one to the corresponding 17(20)Z-ethylidene compound, following the procedure described by Krubiner and Oliveto, *J. Org. Chem.* 31, pp. 24–26 [1965]. Alternatively, the corresponding E-isomer may be obtained following the procedure of Midland and Kwon, *Tetrahedron Lett.* 23(20), pp. 2077–2080 [1982]. The thus-obtained alkenes may be subjected to conventional stereospecific hydroboration reactions followed by oxidative work-up with alkaline hydrogen peroxide solution (Krubiner, op. cit.) to afford the corresponding 20-ols, which may be oxidised to 20-ones with chromium trioxide (Krubiner, op. cit.). Wittig reaction with methoxymethylenetriphenyl-phosphorane followed by hydrolysis of the enol ether with aqueous acid gives a non-stereospecific compound (I) in which X is a valence bond and Y is an aldehyde group. Reduction with sodium borohydride gives a corresponding compound of formula (I) wherein X is a valence bond and Y is hydroxymethyl.

Compounds of the invention having a double bond at the 16(17)-position may, for example, be prepared stereospecifically by subjecting the appropriate E- or Z-17(20) ethylidene compound prepared as described above to a stereospecific ene reaction. For example, such ene reactions include treatment with formaldehyde, boron trifluoride and optionally acetic anhydride (Batcho et al., *Helv. Chim. Acta* 64, pp. 1682–1687 [1981]) to form compounds of formula (I) in which X is a valence bond and Y is hydroxymethyl or acetoxymethyl. In an alternative ene reaction, treatment with ethyl propiolate/diethyl aluminium chloride (Dauben and Brookhart, *J. Am. Chem. Soc.* 103, pp. 237–238 [1980]) affords ethyl esters of Δ16,17 acids which may be reduced to give compounds in which Y is hydroxymethyl. Where appropriate the Δ16,17 compounds described above may be stereospecifically hydrogenated, e.g. catalytically, to form a single bond at the 16(17)-position.

The acetyl group in compounds in which Y is acetoxymethyl may be removed by hydrolysis and replaced by a leaving group such as tosyloxy. Homologation reactions may then be performed to increase the size of X, these including (i) treatment with a metal cyanide, hydrolysing the cyano group to yield a carboxy group or reducing the cyano group (e.g. with a metal hydride reducing agent such as diisobutyl aluminium hydride) to yield a carboxaldehyde group, and where appropriate reducing the carboxy or carboxaldehyde group (e.g. using sodium borohydride or lithium aluminium hydride) to yield a hydroxymethyl group which may in turn be subjected to tosylation and, if desired, further nucleophilic displacement; and (ii) treatment with a metallated derivative of an ester or thioester of acetic acid, with a derivative containing another carbanionic equivalent of acetic acid (e.g. a metallated derivative of acetonitrile), or with a metallated malonate ester (in which last instance the reaction product is partially hydrolysed to yield a monoester which may be decarboxylated by heating to yield a carboxylate ester), reducing the resulting ester or thioester product to an alcohol (e.g. using lithium aluminium hydride), and converting the resulting hydroxyl group to a leaving group, such as a tosylate group or a halogen atom, e.g. as hereinbefore described. Alternatively, compounds in which Y is a carboxaldehyde group may be homologated by Wittig reaction with methoxymethylenetriphenyl-phosphorane followed by hydrolysis of the resulting enol ether, e.g. with aqueous acid.

It will be appreciated that such procedures may be repeated as needed to yield compounds (I) in which X is a desired alkylene group.

Compounds where Y is a group —C($R^4$)($R^5$)$OR^1$ in which $R^4$ and/or $R^5$ are other than hydrogen may be prepared by conventional means, for instance from a corresponding aldehyde or ketone by reaction with an appropriate organometallic reagent, for example a Grignard reagent, metal acetylide, alkyl lithium or alkyl silane.

Compounds according to the invention may also be prepared from a 2-unsubstituted oestrogen by building up the desired 17-position side chain and then introducing the desired 2-substituent as a later step, for instance by following the procedures of Cushman et al. (op. cit.). The key 2-formyl compounds used in such procedures are conveniently prepared by formation of a 3-methoxymethyl ether, selective lithiation at the 2-position and formylation with dimethylformamide according to the procedure of Lovely et al. (op. cit.).

Sulphamoyl $R^1$ groups may be introduced by conventional methods such as reaction with an appropriate sulphamoyl chloride in the presence of a mild base, e.g. as described by Schwartz et al. in *Steroids* 61, pp. 710–717 [1996] or as described in WO-A-9933858. If, for example, it is desired selectively to introduce a sulphamoyl group at the 3-position, any hydroxyl group in the 17-position side chain may be protected during sulphamation, for example as a carboxylic ester (e.g. an acetate) or as a silyl ether; such protecting groups may subsequently be removed by hydrolysis without affecting the sulphamoyl group.

In general, O-protecting groups may, for example, be removed by conventional methods such as are well documented in the literature. Thus esterifying acyl groups may be removed by basic hydrolysis, e.g. using an alkali metal alkoxide in an alkanol. Etherifying groups such as silyl groups may be removed by acid hydrolysis or treatment with a fluoride salt, e.g. a tetraalkyl ammonium fluoride. The use of such acid-labile but base-stable protecting groups may be of particular advantage during homologation steps to build up a desired side chain, in view of the strongly basic conditions normally employed for such reactions.

The contents of all documents referred to in this specification are incorporated herein by reference.

The following non-limitative examples serve to illustrate the invention. All temperatures are in ° C.

Preparation 1

2-Methoxy-3-triisopropylsilyloxy-19-nor-pregn-1,3,5(10), 17(20)Z-tetraene

Sodium hydride (294 mg, 50%) in dimethylsulphoxide (6 ml) was stirred at 70° for 1 hour, then cooled to room temperature. Ethyltriphenylphosphonium iodide (2.75 g) in dimethylsulphoxide (10 ml) was added dropwise and the mixture was stirred for 30 minutes. A solution of 2-methoxy-oestrone-3-triisopropylsilyl ether (600 mg, prepared by silylation of the 3-OH compound with triisopropylsilyl chloride and imidazole in dichloromethane overnight at room temperature) in dimethylsulphoxide (10 ml) was added dropwise. The resulting solution was stirred for 30 minutes, whereafter the temperature was raised to 70° and stirring was continued overnight. The reaction mixture was then cooled and worked up. Separation and purification of the products by chromatography gave the title compound (125 mg, see below) and the 3-OH analogue (300 mg): IR (CDCl$_3$) $\nu_{max}$ 1590, 3520 cm$^{-1}$; NMR (CDCl$_3$) $\delta$ 0.9 (s, 18-H's), 1.67 (d, =CH—CH's), 3.8 (s, OCH's), 4.7–5.2 (q, =CHMe), 6.5, 6.7 (s, 1,4-H's).

Silylation of this 3-OH compound (300 mg) as above and purification of the product by chromatography gave the title compound (370 mg): IR (CDCl$_3$) $\nu_{max}$ 1600 cm$^{-1}$; NMR (CDCl$_3$) $\delta$ 0.9 (s, 18-H's), 1.68 (d, =CH—CH's), 3.7 (s, OCH's), 4.7–5.3 (q, =CH—Me), 6.4, 6.6 (s, 1,4-H's).

EXAMPLE 1 a) 2-Methoxy-3-triisopropylsilyloxy-19-nor-chol-1, 3,5(10),16-tetraene-24-carboxylic acid methyl ester [Formula (I): R$^1$=(i-Pr)$_3$Si, R$^2$=CH$_3$O, R$^3$=α-CH$_3$, X=(CH$_2$)$_2$, Y=CO,OCH$_3$, Δ16 Double Bond]

Ethyl aluminium dichloride (1.4 ml, 2.4 mmol, in toluene) was added dropwise to a solution of the product from Preparation 1 above (370 mg) in dichloromethane (4 ml) containing methyl acrylate (144 μl). The resulting mixture was stirred for 4 hours, whereafter further methyl acrylate (144 μl) was added and stirring was continued overnight. The reaction mixture was then worked up and the product was purified by chromatography to give the title compound (345 mg): IR (CDCl$_3$) $\nu_{max}$ 1600, 1720 cm$^{-1}$; NMR (CDCl$_3$) $\delta$ 0.8 (s, 18-H's), 3.6 (s, OCH's), 5.1–5.4 (bs, 16-H's), 6.4, 6.58 (s, 1,4-H's).

b) 2-Methoxy-3-triisopropylsilyloxy-19-nor-chol-1, 3,5(10),16-tetraen-24-ol [Formula (I): R$^1$=(i-Pr)$_3$Si, R$^2$=CH$_3$O, R$^3$=α-CH$_3$, X=(CH$_2$)$_2$, Y=CH$_2$OH, Δ16 Double Bond]

Lithium aluminium hydride (1 ml of a 1M solution in ether) was added dropwise to a solution of the ester from (a) above (265 mg) in ether (5 ml), whereafter the reaction mixture was stirred for 30 minutes, diluted with ether and quenched with wet sodium sulphate, giving crude title compound (248 mg): IR (CDCl$_3$) $\nu_{max}$ 1600, 3380–3660 cm$^{-1}$; NMR (CDCl$_3$) $\delta$ 0.8 (s, 18-H's), 3.3–3.8 (b, HOCH's), 3.7 (s, OCH's), 5.1–5.4 (bs, 16-H's), 6.4, 6.6 (s, 1,4-H's).

c) 2-Methoxy-3-hydroxy-19-nor-chol-1,3,5(10),16-tetraen-24-ol [Formula (I): R$^1$=H, R$^2$=CH$_3$O, R$^3$=α-CH$_3$, X=(CH$_2$)$_2$, Y=CH$_2$OH, Δ16 Double Bond]

The title compound was prepared by desilylating the product of (b) above by treatment with tetrabutylammonium fluoride in tetrahydrofuran at room temperature overnight: IR (CDCl$_3$) $\nu_{max}$ 1590, 3200–3660 cm$^{-1}$; NMR (CDCl$_3$) $\delta$ 0.8 (s, 18-Me), 1.15 (d, 21-Me), 3.4–3.7 (t, 24-OH, OMe), 5.1–5.4 (ea m, 16-H), 6.5–6.63 (m, 1,4-H's).

d) 2-Methoxy-3-triisopropylsilyloxy-19-nor-chol-1, 3,5(10),16-tetraen-24-ol-24-sulphamate ester [Formula (I): R$^1$=(iPr)$_3$Si, R$^2$=CH$_3$O, R$^3$=α-CH$_3$, X=(CH$_2$)$_3$, Y=CH$_2$O, SO$_2$, NH$_2$]

Sulphamoyl chloride (60 mg) was added to a solution of the alcohol from (b) above (55 mg) and dimethylaminopyridine (62 mg) in methylene chloride (2 ml), and the resulting mixture was stirred for 2 hours. Work up and purification by preparative thin layer chromatography gave the title compound (60 mg): IR (CDCl$_3$) $\nu_{max}$ 1600, 3100–3600 cm$^{-1}$; NMR (CDCl$_3$) $\delta$ 0.8 (s, 18-Me), 3.7 (s, OMe), 3.9–4.4 (bt, 24-H's), 4.5–5.0 (b, NH's), 5.1–5.5 (m, 16-H), 6.43, 6.63 (ea s, 1,4-H's).

e) 2-Methoxy-3-hydroxy-19-nor-chol-1,3,5(10), 16-tetraen-24-ol-24-sulphamate ester [Formula (I): R$^1$= H, R$^2$=CH$_3$O, R$^3$=α-CH$_3$, X=(CH$_2$)$_3$, Y= CH$_2$OSO$_2$NH$_2$]

The product from (d) above was desilylated as in (c) above to afford the title compound (39 mg): IR (CDCl$_3$) $\nu_{max}$ 1590, 3200–3600 cm$^{-1}$; NMR (CDCl$_3$) $\delta$ 0.8 (s, 18-Me), 1.08 (d, 21-H's), 3.8 (s, OMe), 3.9–4.4 (bt, 24-H's), 4.5–4.9 (b, NH's), 4.9–5.5 (m, 16-H), 6.53, 6.67 (ea s, 1,4-H's).

EXAMPLE 2 a) 2-Methoxy-3-triisopropylsilyloxy-20α-acetoxymethyl-19-nor-pregna-1,3,5(10),16-tetraene [Formula (I): R$^1$=(i-Pr)$_3$Si, R$^2$=CH$_3$O, R$^3$=α-CH$_3$, X=Valence Bond, Y=CH$_2$OCOCH$_3$, Δ16 Double Bond]

A mixture of boron trifluoride etherate (6 μl) and acetic anhydride (0.66 ml) in dichloromethane (0.3 ml) was added dropwise to a solution of 2-methoxy-3-triiso-propylsilyloxy-19-nor-pregn-1,3,5(10),17(20)Z-tetraene from Preparation 1 (0.20 g) in dichloromethane (1 ml) containing acetic anhydride (0.1 ml) and paraformaldehyde (13 mg). The mixture was stirred for 2 hours, whereafter saturated sodium hydrogen carbonate was added and stirring was continued for 3 hours. The product was isolated by extraction into dichloromethane and purified by chromatography to give the title compound (205 mg): IR (CDCl$_3$) $\nu_{max}$ 1605, 1725 cm$^{-1}$; NMR (CDCl$_3$) $\delta$ 0.73 (s, 18-H's), 1.97 (s, OCOCH's), 3.6 (s, OCH's), 3.7–4.3 (b, 22-H's), 5.2–5.5 (bs, 16-H's), 6.4, 6.57 (s, 1,4-H's).

b) 2-Methoxy-3-triisopropylsilyloxy-20α-acetoxymethyl-19-nor-pregn-1,3,5(10)-triene [Formula (I): R$^1$=(i-Pr)$_3$Si, R$^2$=CH$_3$O, R$^3$=α-CH$_3$, X=Valence Bond, Y=CH$_2$OCOCH$_3$]

A solution of the product from (a) above (205 mg) in ethanol (5 ml) containing 5% platinum on carbon (40 mg)

was stirred under hydrogen for 18 hours. Filtration and removal of the solvent afforded the title compound mixed with unreacted starting material (195 mg): IR (CDCl$_3$) $v_{max}$ 1600, 1720 cm$^{-1}$; NMR (CDCl$_3$) δ 0.73 (s, 18-H's [starting material]), 0.8 (s, 18-H's [product]), 2.0 (s, OCOCH's), 3.6 (s, OCH's), 3.4–4.3 (b, 22-H's), 5.1–5.5 (bs, 16-H's), 6.4, 6.6 (s, 1,4-H's).

c) 2-Methoxy-3-triisopropylsilyloxy-20α-hydroxymethyl-19-nor-pregn-1,3,5(10)-triene [Formula (I): R$^1$=(i-Pr)$_3$Si, R$^2$=CH$_3$O, R$^3$=α-CH$_3$, X=Valence Bond, Y=CH$_2$OH] and 2-methoxy-3-triisopropylsilyloxy-20α-hydroxymethyl-19-nor-pregn-1,3,5(10),16-tetraene [Formula (I): R$^1$=(i-Pr)$_3$Si, R$^2$=CH$_3$O, R$^3$=α-CH$_3$, X=Valence Bond, Y=CH$_2$OH, Δ16 Double Bond]

Lithium aluminium hydride (0.5 ml of a 1M solution in ether) was added dropwise to the product mixture from (b) above (195 mg) in ether (4 ml). The resulting mixture was stirred for 30 minutes, treated with wet sodium sulphate and worked up to give a crude mixture of the title compounds (175 mg): IR (CDCl$_3$) $v_{max}$ 1600, 3620 cm$^{-1}$; NMR (CDCl$_3$) δ 0.73 (s, 18-H's [starting material]), 0.8 [s, 18-H's [products, ca. 1:1 mixture]), 3.7 (s, OCH's), 3.2–3.7 (b, 22-H's), 5.1–5.5 (bs, 16-H's), 6.4, 6.6 (s, 1,4-H's).

d) 2-Methoxy-3-hydroxy-20α-hydroxymethyl-19-nor-pregn-1,3,5(10)-triene [Formula (I): R$^1$=H, R$^2$=CH$_3$O, R$^3$=α-CH$_3$, X=Valence Bond, Y=CH$_2$OH] and 2-methoxy-3-hydroxy-20α-hydroxymethyl-19-nor-pregn-1,3,5(10),16-tetraene [Formula (I): R$^1$=H, R$^2$=CH$_3$O, R$^3$=α-CH$_3$, X=Valence Bond, Y=CH$_2$OH, Δ16 Double Bond]

The product mixture from (c) above (45 mg) in tetrahydofuran (0.3 ml) was desilylated by treatment with tetrabuylammonium fluoride in tetrahydrofuran (0.3 ml) at room temperature overnight to give the title compound: (28 mg, semi-purified by preparative thin layer chromatrography): IR (CDCl$_3$) $v_{max}$ 1600, 3400–3660 cm$^{-1}$; NMR (CDCl$_3$) δ 0.73 (s, 18-H's [starting material]), 0.83 (s, 18-H's [products, ca. 1:1 mixture]), 3.8 (s, OCH's), 3.2–3.7 (b, 22-H's), 5.2–5.5 (bs, 16-H's), 6.4, 6.63 (s, 1,4-H's).

EXAMPLE 3

2-Methoxy-3-hydroxy-20α-hydroxymethyl-19-nor-pregn-1,3,5(10),16-tetraene [Formula (I): R$^1$=H, R$^2$=CH$_3$O, R$^3$=α-CH$_3$, X=Valence Bond, Y=CH$_2$OH, Δ16 Double Bond]

The title compound was prepared from the product of Example 2(a) by the procedures of Example 2(c) and (d): IR (CDCl$_3$) $v_{max}$ 1580, 3420–3660 cm$^{-1}$; NMR (CDCl$_3$) δ 0.83 (s, 18-Me), 1.07 (d, 21-Me), 3.3–4.0 (bm, 22-H's), 3.8 (s, OMe), 5.1–5.6 (bm, 16-H, OH), 6.47, 6.6 (2×d, 1,4-H's).

EXAMPLE 4

2-Methoxy-3-hydroxy-20α-acetoxymethyl-19-nor-pregn-1,3,5(10),16-tetraene [Formula (I): R$^1$=H, R$^2$=CH$_3$O, R$^3$=α-CH$_3$, X=Valence Bond, Y=CH$_2$O, CO, CH$_3$, Δ16 Double Bond]

The title compound was prepared by desilylating the product of Example 2(a) using the procedure of Example 2(d): IR (CDCl$_3$) $v_{max}$ 1580, 3420–3660 cm$^{-1}$; NMR (CDCl$_3$) δ 0.77 (s, 18-Me), 1.05 (d, 21-Me), 2.0 (s, COMe), 3.2–4.3 (bm, 22-H's), 3.8 (s, OMe), 5.0–5.6 (bm, 16-H, OH), 6.47, 6.6 (2×d, 1,4-H's).

EXAMPLE 5

2-Methoxy-3-hydroxy-20α-hydroxymethyl-19-nor-pregn-1,3,5(10)-triene [Formula (I): R$^1$=H, R$^2$=CH$_3$O, R$^3$=α-CH$_3$, X=Valence Bond, Y=CH$_2$OH]

A solution of the product from Example 3 (60 mg) in ethanol (6 ml) containing 5% platinum on charcoal (20 mg) was stirred under hydrogen overnight, whereafter the catalyst was removed by filtration, the solvent was evaporated and the thus-obtained crude product was purified by preparative thin layer chromatography to give the title compound (44 mg): IR (CDCl$_3$) $v_{max}$ 1580, 3420–3640 cm$^{-1}$; NMR (CDCl$_3$) δ 0.73 (s, 18-Me), 1.07 (d, 21-Me), 3.3–3.7 (bm, 22-H's), 3.83 (s, OMe), 6.5, 6.63 (2×d, 1,4-H's).

EXAMPLE 6 a) 2-Methoxy-3-hydroxy-20α-acetoxymethyl-9-nor-pregn-1,3,5(10),16-tetraene-3-O-sulphamate [Formula (I): R$^1$=NH$_2$, SO$_2$, R$^2$=CH$_3$O, R$^3$=α-CH$_3$, X=Valence Bond, Y=CH$_2$O, CO, CH$_3$, Δ16 Double Bond]

Sulphamoyl chloride (130 mg) was added to a solution of the product from Example 4 (84 mg) and di-tert.-butylaminopyridine (134 mg) in methylene chloride (5 ml), and the resulting mixture was stirred overnight. The mixture was then diluted with ether, washed with water then brine, and dried, whereafter the solvent was removed and the crude product was purified by preparative thin layer chromatography to give unreacted starting material (14 mg) and the title compound (61 mg): IR (CDCl$_3$) $v_{max}$ 1600, 1715, 3200–3500 cm$^{-1}$; NMR (CDCl$_3$) δ 0.8 (s, 18-Me), 2.0 (s, COMe), 3.6–4.3 (bm, 22-H's, OMe), 5.1–5.4 (bm, 16-H, OH), 6.77, 6.9 (2×d, 1,4-H's).

b) 2-Methoxy-3-hydroxy-20α-acetoxymethyl-19-nor-pregn-1,3,5(10)-triene-3-O-sulphamate [Formula (I): R$^1$=NH$_2$, SO$_2$, R$^2$=CH$_3$O, R$^3$=α-CH$_3$, X=Valence Bond, Y=CH$_2$O, CO, CH$_3$]

The title compound is prepared by desilylating the product of Example 2(b) in accordance with the method of Example 2(d) and sulphamoylating the thus obtained 3-hydroxy compound as in (a) above. Alternatively the product of (a) above may be hydrogenated in accordance with the method of Example 2(b).

EXAMPLE 7 a) 2-Methoxy-3-hydroxy-20α-hydroxymethyl-19-nor-pregn-1,3,5(10),16-tetraene-3-O-sulphamate [Formula (I): R$^1$=NH$_2$, SO$_2$, R$^2$=CH$_3$O, R$^3$=α-CH$_3$, X=Valence Bond, Y=CH$_2$OH, Δ16 Double Bond]

The product from Example 6(a) (40 mg) in methanol (3 ml) amd water (1 ml) containing sodium bicarbonate (38 mg) was stirred overnight. Work up and purification by preparative thin layer chromatography gave the title compound (16 mg): IR (CDCl$_3$) $v_{max}$ 3200–3600 cm$^{-1}$; NMR (CDCl$_3$) δ 0.83 (s, 18-Me), 3.3–3.83 (bm, 22-H's, OMe), 4.1–4.8 (bm), 5.2–5.6 (bm, 16-H, OH), 6.4, 7.1 (2×d, 1,4-H's).

b) 2-Methoxy-3-hydroxy-20α-hydroxymethyl-19-nor-pregn-1,3,5(10)-triene-3-O-sulphamate [Formula (I): R$^1$=NH$_2$, SO$_2$, R$^2$=CH$_3$O, R$^3$=α-CH$_3$, X=Valence Bond, Y=CH$_2$OH]

The title compound is prepared by hydrolysing the product of Example 6(b) using the method of (a) above or by hydrogenating the product of (a) above using the method of Example 2(b).

EXAMPLE 8 a) 3-Hydroxy-20α-hydroxymethyl-19-nor-pregn-1,3,5(10)-triene-3,22-bis-methoxymethyl ether [Formula (I): $R^1=CH_3OCH_2$, $R^2=H$, $R^3=\alpha\text{-}CH_3$, X=Valence Bond, $Y=CH_2OCH_2OCH_3$]

The corresponding 3,22-diol (850 mg), which may be prepared by desilylating the product of Preparation 3(b) of WO-A-0068246, was dissolved in tetrahydrofuran (23 ml) containing diisopropylethylamine (3.9 ml) and was treated in the cold (0°) with methoxymethyl chloride (1 ml) added dropwise. The resulting mixture was allowed to warm to room temperature and was then refluxed overnight. Work up and purification by chromatography gave the title compound (900 mg): IR $(CDCl_3)$ $\nu_{max}$ 1600 cm$^{-1}$; NMR $(CDCl_3)$ δ 0.7 (s, 18-Me), 1.08 (d, 21-Me), 3.27, 3.37 (ea s, OMe), 4.5, 5.0 (ea s, OCH$_2$O), 6.5–7.3 (m, 1,2,4-H's).

b) 2-Formyl-3-hydroxy-20α-hydroxymethyl-19-nor-pregn-1,3,5(10)-triene-3,22-bis-methoxymethyl ether [Formula (I): $R^1=CH_3OCH_2$, $R^2=H$, CO, $R^3=\alpha\text{-}CH_3$, X=Valence Bond, $Y=CH_2OCH_2OCH_3$]

A solution of s-butyl lithium in tetrahydrofuran (3.3 ml, 4.3 mM) was added dropwise at −78° to a solution of the ether from (a) above (440 mg) in tetrahydrofuran (6.6 ml). The resulting solution was stirred at −78° for 2 hours, treated with anhydrous dimethylformamide (2 ml) and then allowed to warm to room temperature overnight. Work up and purification by chromatography gave the title compound (323 mg): IR $(CDCl_3)$ $\nu_{max}$ 1600, 1730 cm$^{-1}$; NMR $(CDCl_3)$ δ 0.7 (s, 18-Me), 1.08 (d, 21-Me), 3.3, 3.43 (ea s, OMe), 4.5, 5.13 (ea s, OCH$_2$O), 6.73, 7.57 (ea s, 1,4-H's), 10.2 (s, O=CH).

c) 2,3-dihydroxy-20α-hydroxymethyl-19-nor-pregn-1,3,5(10)-triene-3,22-bis-methoxymethyl ether [Formula (I): $R^1=CH_3OCH_2$, $R^2=HO$, $R^3=\alpha\text{-}CH_3$, X=Valence Bond, $Y=CH_2OCH_2OCH_3$]

A solution of m-chloroperbenzoic acid (204 mg) in methylene chloride (2 ml) was added dropwise to a solution of the formyl compound from (b) above (220 mg) in methylene chloride (4 ml) containing disodium hydrogen phosphate (245 mg). The mixture was stirred overnight at room temperature and was then worked up to give a 2-formate intermediate product. This intermediate was dissolved in methanol (4 ml) and the solution was deoxygenated with argon. Aqueous sodium hydroxide (1 ml, 1M) was added and the resulting solution was stirred for 2 hours and then brought to pH 7. Work up and purification by preparative thin layer chromatography gave the title compound (152 mg): IR $(CDCl_3)$ $\nu_{max}$ 1590, 3200–3600 cm$^{-1}$; NMR $(CDCl_3)$ δ 0.7 (s, 18-Me), 1.14 (d, 21-Me), 3.27, 3.42 (ea s, OMe), 4.5, 5.0 (ea s, OCH$_2$O), 5.5–5.7 (bm, OH), 6.5, 6.9 (ea s, 1,4-H's).

d) 2-Ethoxy-3-hydroxy-2α-hydroxymethyl-19-nor-pregn-1,3,5(10)-triene-3,22-bis-methoxymethyl ether [Formula (I): $R^1=CH_3OCH_2$, $R^2=C_2H_5O$, $R^3=\alpha\text{-}CH_3$, X=Valence Bond, $Y=CH_2OCH_2OCH_3$]

A solution of the 2-hydroxy compound from (c) above (90 mg) in anhydrous dimethylformamide (2.5 ml) containing anhydrous potassium carbonate (300 mg) was stirred for 10 minutes then treated with ethyl iodide (378 mg) followed by tetrabutylammonium iodide (4 mg). The resulting mixture was stirred for a further 5 hours, whereafter more tetrabutylammonium iodide (378 mg) was added and the mixture was stirred overnight. Work up and purification by preparative thin layer chromatography gave the title compound (72 mg): IR $(CDCl_3)$ $\nu_{max}$ 1590 cm$^{-1}$; NMR $(CDCl_3)$ δ 0.73 (s, 18-Me), 1.1 (d, 21-Me), 1.4 (t, Et), 3.35, 3.5 (ea s, OMe), 3.7–4.7 (q, Et), 4.58, 5.08 (ea s, OCH$_2$O), 5.5–5.7 (bm, OH), 6.75 (s, 1,4-H's).

e) 2-Ethoxy-3-hydroxy-20α-hydroxymethyl-19-nor-pregn-1,3,5(10)-triene [Formula (I): $R^1=H$, $R^2=C_2H_5O$, $R^3=\alpha\text{-}CH_3$, X=Valence Bond, $Y=CH_2OH$]

The bis-ether from (d) above (72 mg) in tetrahydrofuran, (1.6 ml) containing hydrochloric acid (0.8 ml, 6N) was stirred at room temperature for 2 days, after which time starting material was still observed to be present. Work up and purification by preparative thin layer chromatography gave unreacted starting material (25 mg) and the title compound (20 mg): NMR $(CDCl_3)$ δ 0.72 (s, 18-Me), 3.2–3.7 (bm, 22-H's), 3.7–4.3 (q, Et), 5.2–5.5 (bm, OH), 6.47, 6.61 (ea s, 1-, 4-H's).

f) 2-Formyl-3-hydroxy-20α-hydroxymethyl-19-nor-pregn-1,3,5(10)-triene [Formula (I): $R^1=H$, $R^2=H$, CO, $R^3=\alpha\text{-}CH_3$, X=Valence Bond, $Y=CH_2OH$]

A solution of the formyl compound from (b) above (100 mg) in tetrahydrofuran (2 ml) was treated with hydrochloric acid (6 ml, 6N) and the mixture was stored for 2 days at room temperature, after which time starting material was observed still to be present. Work up and purification by preparative thin layer chromatography gave the title compound (54 mg): IR $(CDCl_3)$ $\nu_{max}$ 1600, 1650, 3100–3660 cm$^{-1}$; NMR $(CDCl_3)$ δ 0.8 (s, 18-Me), 3.2–3.9 (m, 22-H's), 6.6–7.2 (ea s, 1,4-H's), 9.63 (s, O=CH).

g) 2-Hydroxymethyl-3-hydroxy-20α-hydroxymethyl-19-nor-pregn-1,3,5(10)-triene [Formula (I): $R^1=H$, $R^2=HOCH_2$, $R^3=\alpha\text{-}CH_3$, X=Valence Bond, $Y=CH_2OH$]

Lithium aluminium hydride (0.75 ml of a 1M solution in tetrahydrofuran) was added dropwise to a solution of the 2-formyl compound from (f) above (32 mg) in tetrahydrofuran (1.5 ml) at 0°. The resulting solution was allowed to warm to room temperature and was then stirred for 3 hours. Work up and purification by preparative thin layer chromatography gave the title compound (10 mg): IR $(CDCl_3)$ $\nu_{max}$ 3500–3660 cm$^{-1}$; NMR $(CDCl_3)$ δ 0.73 (s, 18-Me), 3.2–3.8 (m, 22-H's), 4.4–4.8 (bm, 2-CH$_2$OH), 6.6–7.2 (ea s, 1,4-H's).

h) 2-Propenyl-3-hydroxy-20α-hydroxymethyl-19-nor-pregn-1,3,5(10)-triene [Formula (I): $R^1=H$, $R^2=CH_3$, CH=CH, $R^3=\alpha\text{-}CH_3$, X=Valence Bond, $Y=CH_2OH$]

The title compound is obtained by adding a solution of the 2-formyl compound from (f) above in tetrahydrofuran to a solution of the ylide formed by reacting ethyltriphenylphosphonium bromide in tetrahydrofuran with lithium bis-trimethylsilylamide. Alternatively the protected 2-formyl compound from (b) above may be reacted with the same ylide, followed by removal of the methoxymethyl protecting groups as in (f) above.

EXAMPLE 9 a) 2-Methoxy-3-triisopropylsilyloxy-20α-hydroxymethyl-19-nor-pregn-1,3,5, (10)-triene [Formula (I): $R^1=(i\text{-}Pr_3)Si$, $R^2=CH_3O$, $R^3=\alpha\text{-}CH_3$, X=Valence Bond, $Y=CH_2OH$]

The 20α-acetoxymethyl product from Example 2(a) (360 mg) was first deacetylated by treatment with lithium aluminium hydride (1.2 ml, 2.5 eq.) in ether (7 ml) for 30 minutes at room temperature. The thus-obtained crude 20α-hydroxymethyl compound (200 mg) was then hydrogenated over 5% platinum on carbon (40 mg) in ethanol (10 ml). Filtration and removal of the solvent gave the title compound (175 mg): IR (CDCl$_3$) $\nu_{max}$ 1600, 3300–3640 cm$^{-1}$; NMR (CDCl$_3$) δ 0.73 (s, 18-Me), 3.1–3.5 (m, 22-H; s, OMe), 6.43, 6.6(ea s, 1,4-H's).

b) 2-Methoxy-3-triisopropylsilyloxy-19-nor-pregn-1, 3,5, (10)-triene-20α-carboxaldehyde [Formula (I): R$^1$=(i-Pr$_3$)Si, R$^2$=CH$_3$O, R$^3$=α-CH$_3$, X=Valence Bond, Y=CHO]

The alcohol from (a) above (175 mg) in methylene chloride (4 ml) was treated with pyridinium dichromate (165 mg) for 2.5 hours. As the reaction was observed to be incomplete (50%, thin layer chromatography control) further pyridinium dichromate (165 mg) was added and the reaction mixture was stirred for a further 2.5 hours, by which time most of the starting material was observed to have been consumed. Work up and purification by preparative thin layer chromatography gave the title compound (125 mg): IR (CDCl$_3$) $\nu_{max}$ 1600, 1710 cm$^{-1}$; NMR (CDCl$_3$) δ 0.73 (s, 18-Me), 3.67 (s, OMe), 6.4, 6.6 (ea s, 1,4-H's), 9.38 (d, CH=O).

c) 2-Methoxy-3-triisopropylsilyloxy-20α-(1-hydroxyethyl)-19-nor-pregn-1,3,5(10)-triene [Formula (I): R$^1$=(i-Pr$_3$)Si, R$^2$=CH$_3$O, R$^3$=α-CH$_3$, X=Valence Bond, Y=CH(CH$_3$)OH]

Methyl magnesium bromide (0.53 ml of a 1.4M solution in tetrahydrofuran/toluene) was added dropwise to a solution of the aldehyde from (b) above (125 mg) in ether at 0°. After 30 minutes at 0° and 30 minutes at room temperature the reaction was terminated by addition of saturated aqueous ammonium chloride and the product was worked up to give the title compound (125 mg): IR (CDCl$_3$) $\nu_{max}$ 1590, 3500–3640 cm$^{-1}$; NMR (CDCl$_3$) δ 0.7 (s, 18-Me), 3.3–3.67 (m, CHOH; s, OMe), 6.4, 6.6 (ea s, 1,4-H's).

d) 2-Methoxy-3-hydroxy-20α-(1-hydroxyethyl)-19-nor-pregn-1,3,5(10)-triene [Formula (I): R$^1$=H, R$^2$=CH$_3$O, R$^3$=α-CH$_3$, X=Valence Bond, Y=CH(CH$_3$)OH]

The product from (c) above (45 mg) was desilylated by treatment with tetrabutylammonium fluoride (0.3 ml) in tetrahydrofuran (0.3 ml) (thin layer chromatography control, about 4 hours). Work up and purification by preparative thin layer chromatography gave the title compound (24 mg): IR (CDCl$_3$) $\nu_{max}$ 1580, 3460–3640 cm$^{-1}$; NMR (CDCl$_3$) δ 0.75 (s, 18-Me), 1.05 (d, 21-Me), 3.4–4.1 (m, CHOH; s, OMe), 6.5, 6.65 (ea s, 1,4-H's).

e) 2-Methoxy-3-hydroxy-2α-(1-hydroxyprop-2-ynyl)-19-nor-pregn-1,3,5(10)-triene [Formula (I): R$^1$=H, R$^2$=CH$_3$O, R$^3$=α-CH$_3$, X=Valence Bond, Y=—CH(OH)C≡CH]

The title compound is prepared by treatment of the aldehyde from (b) above with sodium acetylide, followed by desilylation as in (d) above.

f) 2-Methoxy-3-hydroxy-20α-(1-hydroxybut-3-ynyl)-19-nor-pregn-1,3,5(10)-triene [Formula (I): R$^1$=H, R$^2$=CH$_3$O, R$^3$=α-CH$_3$, X=Valence Bond, Y=CH(OH)CH$_2$C≡CH]

The title compound is prepared by treatment of the aldehyde from (b) above with propargyl aluminium reagent prepared as described in Example 3(b) of WO-A-0068246, followed by desilylation as in (d) above.

g) 22-Methoxy-3-hydroxy-20α-(2-hydroxyprop-2-yl)-19-nor-pregn-1,3,5(10)-triene [Formula (I): R$^1$=H, R$^2$=CH$_3$O, R$^3$=α-CH$_3$, X=Valence Bond, Y=—C(OH)(CH$_3$)$_2$]

The title compound is obtained by oxidation of the 20α-(1-hydroxyethyl) compound from (c) above using pyridinium dichromate in accordance with the method of (b) above, followed by reaction with methyl magnesium bromide as in (c) above and desilylation as in (d) above.

h) 2-Methoxy-3-triisopropylsilyloxy-19-nor-pregn-1, 3,5(10)-triene-20β-carboxaldehyde [Formula (I) R$^1$=(i-Pr$_3$)Si, R$^2$=CH$_3$O, R$^3$=β-CH$_3$, X=Valence Bond, Y=CHO]

The title compound was obtained by isomerisation of the aldehyde from (b) above by treatment with 1,8-diazabicyclo[5.4.0]undec-7-ene in similar manner to that described in Preparation 5 of WO-A-9516672 and isolation of the newly formed isomer by chromatography (silica gel G, toluene/hexane, more polar isomer).

i) 2-Methoxy-3-hydroxy-19-nor-pregn-1,3,5(10)-triene-20β-carboxaldehyde [Formula (I): R$^1$=H, R$^2$=CH$_3$O, R$^3$=β-CH$_3$, X=Valence Bond, Y=CHO]

The title compound is formed by desilylation of the epi-aldehyde from (h) above in accordance with the method of (d) above.

j) 2-Methoxy-3-hydroxy-20β-hydroxymethyl-19-nor-pregn-1,3,5(10)-triene [Formula (I): R$^1$=H, R$^2$=CH$_3$O, R$^3$=β-CH$_3$, X=Valence Bond, Y=CH$_2$OH]

The title compound is obtained by reduction of the epi-aldehyde product from (h) above with sodium borohydride, followed by desilylation as in (d) above.

k) 2-Methoxy-3-triisopropylsilyloxy-20α-(2-oxoethyl)-19-nor-pregn-1,3,5(10)-triene [Formula (I): R$^1$=(i-Pr$_3$)Si, R$^2$=CH$_3$O, R$^3$=α-CH$_2$, Y=CHO]

The title compound is prepared from the aldehyde product of (b) above by reaction with methoxymethylenetriphenylphosphorane followed by acid hydrolysis of the intermediate enol ether, in similar manner to that described in Preparation 1 of WO-A-9945024.

l) 2-Methoxy-3-hydroxy-20α-(2-oxoethyl)-19-nor-pregn-1,3,5(10)-triene (Formula (I): R$^1$=H, R$^2$=CH$_3$O, R$^3$=α-CH$_3$, X=CH$_2$, Y=CHO]

The title compound is prepared by desilylation of the product of (k) above as in (d) above.

m) 2-Methoxy-3-hydroxy-20α-(2-hydroxyethyl)-19-nor-pregn-1,3,5(10)-triene [Formula (I): R$^1$=H, R$^2$=CH$_3$O, R$^3$=α-CH$_3$, X=CH$_2$, Y=CH$_2$OH]

The title compound is prepared by reduction of the aldehyde product of (k) above with sodium borohydride, followed by desilylation as in (d) above.

EXAMPLE 10

2-Methoxy-3-hydroxy-20α-hydroxymethyl-19-nor-pregn-1,3,5(10),16-tetraene-3,22-bis-O-sulphamate [Formula (I): R$^1$=NH$_2$, SO$_2$, R$^2$=CH$_3$O, R$^3$=α-CH$_3$, X=Valence Bond, Y=CH$_2$OSO$_2$NH$_2$, Δ16 Double Bond]

Sulphamoyl chloride (62 mg) was added to a solution of the product from Example 3 (16 mg) and dimethylaminopyridine (60 mg) in methylene chloride (1 ml), and the resulting mixture was stirred overnight. The mixture was then diluted with ether, washed with water then brine, and dried, whereafter the solvent was removed and the crude product was purified by preparative thin layer chromatography to give the title compound (10 mg): IR (CDCl$_3$) $v_{max}$ 1620, 3100–3600 cm$^{-1}$; NMR (CDCl$_3$) δ 0.8 (s, 18-Me), 1.12 (d, 21-Me), 3.77 (OMe), 5.0–5.5 (bm, 16-H), 6.73, 6.87 (ea s, 1,4-H's).

EXAMPLE 11 a) 2-Methoxy-3-triisopropylsilyloxy-20α-hydroxymethyl-19-nor-pregn-1,3,5(10),16-tetraene-22-O-sulphamate [Formula (I): R$^1$=(i-Pr$_3$)Si, R$^2$=CH$_3$O, R$^3$=α-CH$_3$, X=Valence Bond, Y=CH$_2$OSO$_2$NH$_2$, Δ16 Double Bond]

Sulphamoyl chloride (60 mg) was added to a solution of 2-methoxy-3-triisopropylsilyloxy-20α-hydroxymethyl-19-nor-pregn-1,3,5(10),16-tetraene [Formula (I): R$^1$=(i-Pr$_3$)Si, R$^2$=CH$_3$O, R$^3$=α-CH$_3$, X=valence bond, Y=CH$_2$OH, Δ16 double bond, obtained from the first step of Example 9(a)] (50 mg) and dimethylaminopyridine (60 mg) in methylene chloride (2.5 ml) and the resulting mixture was stirred for 1 hour. The mixture was then diluted with ether, washed with water then brine, and dried, whereafter the solvent was removed and the crude product was purified by preparative thin layer chromatography to give the title compound (55 mg): IR (CDCl$_3$) $v_{max}$ 1590, 3200–3500 cm$^{-1}$; NMR (CDCl$_3$) δ 0.83 (s, 18-Me), 3.7 (s, OMe), 4.4–4.8 (bm, NH's), 5.2–5.5 (bm, 16-H), 6.4, 6.6 (ea s, 1,4-H's).

b) 2-Methoxy-3-hydroxy-20α-hydroxymethyl-19-nor-pregn-1,3,5(10),16-tetraene-22-O-sulphamate [Formula (I): R$^1$=H, R$^2$=CH$_3$O, R$^3$=α-CH$_3$, X=Valence Bond, Y=CH$_2$OSO$_2$NH$_2$, Δ16 Double Bond]

The silyl ether from (a) above (55 mg) was desilylated by treatment with tetrabutylammonium fluoride in tetrahydrofuran at room temperature for 3 hours and worked up and purified by preparative thin layer chromatography to give the title compound (30 mg): IR (CDCl$_3$) $v_{max}$ 1590, 3200–3600 cm$^{-1}$.

What is claimed is:
1. Compounds of formula (I)

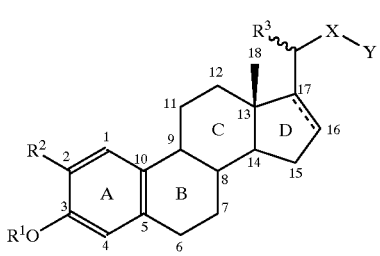

(I)

in which:
R$^1$ represents a hydrogen atom or an O-protecting group;
R$^2$ represents a hydroxyl, lower alkoxy, carboxaldehyde, lower alk-1-enyl or hydroxy- or lower alkoxy-substituted lower alkyl group;
R$^3$ represents a methyl group having α- or β-configuration;
X represents a C$_{1-3}$ alkylene group or a valence bond;

Y represents a carboxaldehyde group or a group of formula —C(R$^4$)(R$^5$)OR$^1$ where R$^1$ is as defined above and R$^4$ and R$^5$, which may be the same or different, are each selected from hydrogen atoms, alkyl, alkenyl and alkynyl groups such that the total carbon content of R$^4$ and R$^5$ does not exceed three atoms, with the proviso that X is a valence bond when both R$^4$ and R$^5$ are other than hydrogen; and
the dotted line signifies that a double bond may optionally be present at the 16(17)-position.

2. Compounds as claimed in claim 1 wherein R$^2$ represents a hydroxy or lower alkoxy group and Y is a carboxaldehyde group or a group of formula —C(R$^4$)(R$^5$) OR$^1$ where R$^1$ is as defined in claim 1 and R$^4$ and R$^5$ both represent hydrogen atoms.

3. Compounds as claimed in claim 1 wherein Y is a group of formula —C(R$^4$)(R$^5$)OR$^1$ in which R$^1$ is as defined in claim 1, one of R$^4$ and R$^5$ is methyl, ethyl, vinyl, ethynyl or propargyl and the other is hydrogen, or R$^4$ and R$^5$ both represent methyl groups.

4. Compounds as claimed in claim 1 wherein each R$^1$ is selected from hydrogen atoms, lower alkyl groups and metabolically labile O-protecting groups.

5. Compounds as claimed in claim 4 wherein said metabolically labile O-protecting groups are sulphamoyl groups.

6. Compounds as claimed in claim 1 wherein R$^2$ is selected from methoxy, ethoxy, propoxy, vinyl, prop-1-enyl, but-1-enyl, hydroxymethyl, hydroxyethyl, hydroxypropyl, methoxymethyl, methoxyethyl, methoxypropyl, ethoxymethyl, ethoxyethyl and ethoxypropyl groups.

7. The compounds:
2-methoxy-3-hydroxy-19-nor-chol-1,3,5(10),16-tetraen-24-ol;
2-methoxy-3-hydroxy-19-nor-chol-1,3,5(10),16-tetraen-24-ol-24-sulphamate ester;
2-methoxy-3-hydroxy-20α-hydroxymethyl-19-nor-pregn-1,3,5(10)-triene;
2-methoxy-3-hydroxy-20α-hydroxymethyl-19-nor-pregn-1,3,5(10),16-tetraene;
2-methoxy-3-hydroxy-20α-acetoxymethyl-19-nor-pregn-1,3,5(10,16-tetraene;
2-methoxy-3-hydroxy-20α-acetoxymethyl-19-nor-pregn-1,3,5(10),16-tetraene-3-O-sulphamate;
2-methoxy-3-hydroxy-20α-acetoxymethyl-19-nor-pregn-1,3,5(10)-triene-3-O-sulphamate;
2-methoxy-3-hydroxy-20α-hydroxymethyl-19-nor-pregn-1,3,5(10),16-tetraene-3-O-sulphamate;
2-methoxy-3-hydroxy-20α-hydroxymethyl-19-nor-pregn-1,3,5(10 )-triene-3-O-sulphamate;
2-ethoxy-3-hydroxy-20α-hydroxymethyl-19-nor-pregn-1,3,5(10)-triene;
2-hydroxymethyl-3-hydroxy-20α-hydroxymethyl-19-nor-pregn-1,3,5(10)-triene;
2-propenyl-3-hydroxy-20α-hydroxymethyl-19-nor-pregn-1,3,5(10)-triene;
2-methoxy-3-hydroxy-20α-(1-hydroxyethyl)-19-nor-pregn-1,3,5(10)-triene;
2-methoxy-3-hydroxy-20α-(1-hydroxyprop-2-ynyl)-19-nor-pregn-1,3,5(10)-triene;
2-methoxy-3-hydroxy-20α-(1-hydroxybut-3-ynyl)-19-nor-pregn-1,3,5(10-triene;
2-methoxy-3-hydroxy-20α-(2-hydroxyprop-2-yl)-19-nor-pregn-1,3,5(10)-triene;
2-methoxy-3-hydroxy-19-nor-pregn-1,3,5(10)-triene-20β-carboxaldehyde;

2-methoxy-3-hydroxy-20β-hydroxymethyl-19-nor-pregn-1,3,5(1)-triene;

2-methoxy-3-hydroxy-20α-(2-oxoethyl)-19-nor-pregn-1,3,5(10)-triene;

2-methoxy-3-hydroxy-20α-(2-hydroxyethyl)-19-nor-pregn-1,3,5(10)-triene;

2-methoxy-3-hydroxy-20α-hydroxymethyl-19-nor-pregn-1,3,5(10),16-tetraene-3,22-bis-O-sulphamate; and 2-methoxy-3-hydroxy-20α-hydroxymethyl-19-nor-pregn-1,3,5(10),16-tetraene-22-O-sulphamate.

8. Pharmaceutical compositions comprising an active compound of formula (I) as claimed in claim 1 in admixture with one or more physiologically acceptable carriers or excipients.

9. A method of treatment of a human or non-human animal subject in the management of neoplastic disease; to promote wound healing; or in treatment of bone diseases, autoimmune disease, host-graft reaction, transplant rejection, inflammatory diseases, neoplasias or hyperplasias, rheumatoid arthritis, or psoriatic arthritis, which method comprises administering to said subject a therapeutically effective amount of an active compound of formula (I) as claimed in claim 1.

10. A method of inhibiting angiogenesis in a human or non-human animal subject, which method comprises administering to said subject a therapeutically effective amount of an active compound of formula (I) as claimed in claim 1.

* * * * *